(12) United States Patent
Ma

(10) Patent No.: US 9,327,095 B2
(45) Date of Patent: May 3, 2016

(54) BLOOD CONTROL CATHETER WITH ANTIMICROBIAL NEEDLE LUBE

(71) Applicant: Becton, Dickinson and Company, Franklin Lakes, NJ (US)

(72) Inventor: Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/793,569

(22) Filed: Mar. 11, 2013

(65) Prior Publication Data
US 2014/0257234 A1 Sep. 11, 2014

(51) Int. Cl.
*A61M 5/00* (2006.01)
*A61M 31/00* (2006.01)
(Continued)

(52) U.S. Cl.
CPC ............... *A61M 25/002* (2013.01); *A61L 29/14* (2013.01); *A61L 29/16* (2013.01); *A61M 25/0043* (2013.01); *A61M 25/0606* (2013.01); *A61M 39/0606* (2013.01); *A61M 39/162* (2013.01); *A61L 2300/404* (2013.01); *A61L 2400/10* (2013.01); *A61M 25/0045* (2013.01);
(Continued)

(58) Field of Classification Search
CPC ............... A61M 2039/062; A61M 2039/0633; A61M 2039/064; A61M 25/0606; A61M 2039/068; A61M 2025/0056; A61M 2039/066; A61M 2025/0046; A61M 2039/0036; A61M 2205/0205; A61M 2205/0222; A61M 25/002; A61M 25/0043; A61M 25/0045; A61M 25/0097; A61M 2039/0606; A61M 39/162; A61L 2300/404; A61L 2400/10; A61L 29/14; A61L 29/16
USPC .................................. 604/164.01–170.03, 500
See application file for complete search history.

(56) References Cited

U.S. PATENT DOCUMENTS 3,223,629 A 12/1965 Loeffler
4,339,336 A 7/1982 Hammond et al.
(Continued)

FOREIGN PATENT DOCUMENTS

CN 1526771 A 9/2004
CN 101353545 A 1/2009
(Continued)

OTHER PUBLICATIONS

"ComfortCoat Hydrophilic Coating," DSM in Medical, http://www.dsm.com/en_US/medical/public/home/pages/product-coating-comfortcoat.jsp, Updated Jan. 11, 2013, Printed Apr. 22, 2013.
(Continued)

*Primary Examiner* — Jason Flick
(74) *Attorney, Agent, or Firm* — Jeanne Lukasavage; Craig Metcalf; Kirton McConkie

(57) ABSTRACT

An antimicrobial lubricant applied to an outer surface of an introducer needle as part of a catheter assembly device. The catheter assembly device further includes a blood control septum having a slit through which the introducer needle is threaded. The antimicrobial lubricant is squeegeed, or removed from the outer surface of the introducer needle as the needle is removed from the slit following catheterization. The removed antimicrobial lubricant forms a deposit on the septum at a location proximate to the slit, thereby preventing colonization and growth of pathogens on the septum and other adjacent components and surfaces of the catheter assembly device.

20 Claims, 7 Drawing Sheets

(51) Int. Cl.
*A61M 25/00* (2006.01)
*A61L 29/16* (2006.01)
*A61M 25/06* (2006.01)
*A61L 29/14* (2006.01)
*A61M 39/06* (2006.01)
*A61M 39/16* (2006.01)
*A61M 39/00* (2006.01)

(52) U.S. Cl.
CPC .... *A61M25/0097* (2013.01); *A61M 2025/0046* (2013.01); *A61M 2025/0056* (2013.01); *A61M 2039/0036* (2013.01); *A61M 2039/062* (2013.01); *A61M 2039/064* (2013.01); *A61M 2039/068* (2013.01); *A61M 2205/0205* (2013.01); *A61M 2205/0222* (2013.01)

(56) References Cited

U.S. PATENT DOCUMENTS

| | | |
|---|---|---|
| 4,584,192 A | 4/1986 | Dell et al. |
| 4,603,152 A | 7/1986 | Laurin et al. |
| 4,629,743 A | 12/1986 | Hong |
| 4,629,746 A | 12/1986 | Michl et al. |
| 4,642,126 A | 2/1987 | Zador et al. |
| 4,676,782 A | 6/1987 | Yamamoto et al. |
| 4,677,143 A | 6/1987 | Laurin et al. |
| 4,716,032 A | 12/1987 | Westfall et al. |
| 4,798,594 A * | 1/1989 | Hillstead ............... 604/167.04 |
| 4,895,566 A | 1/1990 | Lee |
| 4,915,934 A | 4/1990 | Tomlinson |
| 4,925,668 A * | 5/1990 | Khan et al. ................. 424/422 |
| 4,955,890 A | 9/1990 | Yamamoto et al. |
| 4,985,399 A | 1/1991 | Matsuda et al. |
| 5,023,082 A | 6/1991 | Friedman et al. |
| 5,217,493 A | 6/1993 | Raad et al. |
| 5,366,505 A | 11/1994 | Farber |
| 5,456,948 A | 10/1995 | Mathisen et al. |
| 5,512,199 A | 4/1996 | Khan et al. |
| 5,540,661 A | 7/1996 | Tomisaka et al. |
| 5,547,662 A | 8/1996 | Khan et al. |
| 5,616,338 A | 4/1997 | Fox, Jr. et al. |
| 5,638,812 A | 6/1997 | Turner |
| 5,653,695 A | 8/1997 | Hopkins et al. |
| 5,698,229 A | 12/1997 | Ohsumi et al. |
| 5,712,229 A | 1/1998 | Hopkins et al. |
| 5,716,406 A | 2/1998 | Farber |
| 5,763,412 A | 6/1998 | Khan et al. |
| 5,773,487 A | 6/1998 | Sokol |
| 5,861,440 A | 1/1999 | Gohla et al. |
| 6,051,609 A | 4/2000 | Yu et al. |
| 6,120,784 A | 9/2000 | Snyder, Jr. |
| 6,127,320 A | 10/2000 | van Ooij et al. |
| 6,242,526 B1 | 6/2001 | Siddiqui et al. |
| 6,248,811 B1 | 6/2001 | Ottersbach et al. |
| 6,326,417 B1 | 12/2001 | Jia |
| 6,337,357 B1 | 1/2002 | Fukunishi et al. |
| 6,353,041 B1 | 3/2002 | Qian |
| 6,413,539 B1 | 7/2002 | Shalaby |
| 6,475,434 B1 | 11/2002 | Darouiche |
| 6,488,942 B1 | 12/2002 | Ingemann |
| 6,492,445 B2 | 12/2002 | Siddiqui et al. |
| 6,576,633 B1 | 6/2003 | Young et al. |
| 6,579,539 B2 | 6/2003 | Lawson et al. |
| 6,719,991 B2 | 4/2004 | Darouiche et al. |
| 6,723,350 B2 | 4/2004 | Burrell et al. |
| 6,843,784 B2 | 1/2005 | Modak et al. |
| 6,846,846 B2 | 1/2005 | Modak et al. |
| 6,861,060 B1 | 3/2005 | Luriya et al. |
| 6,887,270 B2 | 5/2005 | Miller et al. |
| 6,896,889 B2 | 5/2005 | Chevalier et al. |
| 7,074,839 B2 | 7/2006 | Fansler et al. |
| 7,098,256 B2 | 8/2006 | Ong et al. |
| 7,179,849 B2 | 2/2007 | Terry |
| 7,198,800 B1 | 4/2007 | Ko |
| 7,232,540 B2 | 6/2007 | Gould et al. |
| 7,261,925 B2 | 8/2007 | Nesbitt |
| 7,268,165 B2 | 9/2007 | Greten et al. |
| 7,407,707 B2 | 8/2008 | Gould et al. |
| 7,462,401 B2 | 12/2008 | Halfyard et al. |
| 7,494,339 B2 | 2/2009 | Dias et al. |
| 7,498,367 B2 | 3/2009 | Qian |
| 7,514,477 B2 | 4/2009 | Klare et al. |
| 7,816,434 B2 | 10/2010 | Hackbarth et al. |
| 8,034,455 B2 | 10/2011 | Wang et al. |
| 8,227,050 B1 | 7/2012 | O'Neil |
| 8,263,102 B2 | 9/2012 | Labrecque et al. |
| 8,388,583 B2 | 3/2013 | Stout et al. |
| 8,414,547 B2 | 4/2013 | DiFiore et al. |
| 2001/0010016 A1 | 7/2001 | Modak et al. |
| 2001/0016589 A1 | 8/2001 | Modak et al. |
| 2001/0056133 A1 | 12/2001 | Montgomery et al. |
| 2002/0009436 A1 | 1/2002 | Doyle et al. |
| 2002/0028751 A1 | 3/2002 | Lokkesmoe et al. |
| 2002/0037260 A1 | 3/2002 | Budny et al. |
| 2002/0040092 A1 | 4/2002 | Siddiqui et al. |
| 2002/0064858 A1 | 5/2002 | Yacoby-Zeevi |
| 2002/0091424 A1 | 7/2002 | Biel |
| 2002/0119111 A1 | 8/2002 | Kilgour et al. |
| 2002/0133124 A1 | 9/2002 | Leinsing et al. |
| 2002/0144705 A1 | 10/2002 | Brattesani et al. |
| 2003/0072781 A1 | 4/2003 | Pelerin |
| 2003/0105143 A1 | 6/2003 | Ammendola et al. |
| 2003/0119932 A1 | 6/2003 | Al-Akhdar et al. |
| 2003/0134783 A1 | 7/2003 | Harshey et al. |
| 2003/0144362 A1 | 7/2003 | Utterberg et al. |
| 2003/0147932 A1 | 8/2003 | Nun et al. |
| 2003/0162839 A1 | 8/2003 | Symington et al. |
| 2003/0170308 A1 | 9/2003 | Cleary et al. |
| 2003/0176848 A1 | 9/2003 | Gibson et al. |
| 2003/0206875 A1 | 11/2003 | Budny et al. |
| 2003/0215433 A1 | 11/2003 | Kokai-Kun et al. |
| 2003/0224032 A1 | 12/2003 | Read et al. |
| 2004/0039349 A1 | 2/2004 | Modak et al. |
| 2004/0058829 A1 | 3/2004 | Hei et al. |
| 2004/0109852 A1 | 6/2004 | Xu |
| 2004/0115477 A1 | 6/2004 | Nesbitt |
| 2004/0132164 A1 | 7/2004 | Doyle et al. |
| 2004/0180829 A1 | 9/2004 | Bassler et al. |
| 2004/0185296 A1 | 9/2004 | Mazzanti |
| 2004/0230162 A1 | 11/2004 | Tan |
| 2004/0234475 A1 | 11/2004 | Lannibois-Drean et al. |
| 2005/0008671 A1 | 1/2005 | Van Antwerp |
| 2005/0048005 A1 | 3/2005 | Stockel |
| 2005/0048124 A1 | 3/2005 | Sarangapani |
| 2005/0059731 A1 | 3/2005 | Albrecht et al. |
| 2005/0100580 A1 | 5/2005 | Osborne et al. |
| 2005/0118239 A1 | 6/2005 | Sabesan |
| 2005/0131356 A1 | 6/2005 | Ash et al. |
| 2005/0143286 A1 | 6/2005 | Singh et al. |
| 2005/0158253 A1 | 7/2005 | Budny et al. |
| 2005/0176905 A1 | 8/2005 | Moon et al. |
| 2005/0233950 A1 | 10/2005 | Madhyastha |
| 2005/0265931 A1 | 12/2005 | Qian |
| 2006/0024372 A1 | 2/2006 | Utterberg et al. |
| 2006/0165751 A1 | 7/2006 | Chudzik et al. |
| 2006/0165903 A1 | 7/2006 | Mazzanti |
| 2006/0239954 A1 | 10/2006 | Sancho |
| 2006/0258780 A1 | 11/2006 | Chaussade et al. |
| 2007/0000407 A1 | 1/2007 | Leong |
| 2007/0112112 A1 | 5/2007 | Kerschner et al. |
| 2007/0112146 A1 | 5/2007 | Falk et al. |
| 2007/0141524 A1 | 6/2007 | Brennan et al. |
| 2007/0160547 A1 | 7/2007 | Duffy et al. |
| 2007/0166344 A1 | 7/2007 | Qu et al. |
| 2007/0202177 A1 | 8/2007 | Hoang |
| 2007/0203574 A1 | 8/2007 | McGrath et al. |
| 2007/0225179 A1 | 9/2007 | Schutz et al. |
| 2007/0275101 A1 | 11/2007 | Lu et al. |
| 2008/0026026 A1 | 1/2008 | Lu et al. |
| 2008/0051737 A1 | 2/2008 | Paul et al. |
| 2008/0075761 A1 | 3/2008 | Modak et al. |
| 2008/0161763 A1 | 7/2008 | Harding et al. |
| 2008/0182921 A1 | 7/2008 | Suh et al. |

(56) References Cited

U.S. PATENT DOCUMENTS

| | | | |
|---|---|---|---|
| 2009/0012220 A1 | 1/2009 | Yamane et al. | |
| 2009/0101152 A1 | 4/2009 | Burk et al. | |
| 2009/0110844 A1 | 4/2009 | Platzer et al. | |
| 2009/0114327 A1 | 5/2009 | Breunig | |
| 2009/0162530 A1 | 6/2009 | Nesbitt | |
| 2009/0176907 A1 | 7/2009 | Subramanian et al. | |
| 2009/0188559 A1 | 7/2009 | Nesbitt | |
| 2009/0220739 A1 | 9/2009 | Chougule | |
| 2010/0135949 A1 | 6/2010 | Ou-Yang | |
| 2010/0136209 A1 | 6/2010 | Ou-Yang et al. | |
| 2010/0137379 A1 | 6/2010 | Ou-Yang | |
| 2010/0137472 A1 | 6/2010 | Ou-Yang | |
| 2010/0204648 A1* | 8/2010 | Stout et al. | 604/122 |
| 2011/0009831 A1 | 1/2011 | Burkholz et al. | |
| 2011/0065798 A1 | 3/2011 | Hoang et al. | |
| 2011/0301553 A1* | 12/2011 | Goral et al. | 604/265 |

FOREIGN PATENT DOCUMENTS

| | | |
|---|---|---|
| DE | 4011867 A1 | 10/1991 |
| EP | 0 036 294 A2 | 9/1981 |
| EP | 0 338 418 A1 | 10/1989 |
| EP | 0 379 271 A2 | 7/1990 |
| EP | 0 396 431 A1 | 11/1990 |
| JP | 05-277434 | 10/1993 |
| JP | 09-151262 | 6/1997 |
| JP | 2002-282762 | 10/2002 |
| JP | 2003-342402 | 3/2003 |
| KR | 20020066429 A | 8/2002 |
| WO | 98/58690 | 12/1998 |
| WO | 98/58989 | 12/1998 |
| WO | 99/32168 | 7/1999 |
| WO | 00/66189 | 11/2000 |
| WO | 2004/108091 A2 | 12/2004 |
| WO | 2006/056482 A1 | 6/2006 |
| WO | 2006/074666 A2 | 7/2006 |
| WO | 2006/099358 A2 | 9/2006 |
| WO | 2007/064835 A2 | 6/2007 |
| WO | 2007/100653 A2 | 9/2007 |
| WO | 2007/100776 A2 | 9/2007 |
| WO | 2008/014447 A2 | 1/2008 |
| WO | 2008/013601 A1 | 3/2008 |
| WO | 2008/031601 A1 | 3/2008 |
| WO | 2008/132045 A2 | 11/2008 |

OTHER PUBLICATIONS

"Lubricent—Lubricious Hydrophillic Coatings for Medical Devices," Harland Medical Systems, http://www.harlandmedical.com/index.php/materials/lubricent.html, pp. 1-2, Printed Apr. 22, 2013.

"UV & EB Cure," Xiper Innovations, Inc., http://xiperinnovations.com/uv_eb_cure, Printed Apr. 22, 2013.

Cabot Corporation, "Using Silicas and Aluminas in Coatings,", www.cabot-corp.com/Silicas-And-Aluminas/Coatings, downloaded from the internet on Apr. 26, 2011.

Gama Healthcare, Clinell Alcoholic 2% Chlorhexidine, http://www.gamahealthcare.com/clinellaca2c.html, pp. 1-3, Nov. 7, 2008.

Sage Products, Inc., Preoperative Skin Preparation for the Surgical Patient, http://www.sageproducts.com/products/skin-prep.cfm, 1 page, Oct. 31, 2008.

Sage Products, Inc., Address Multi-Drug Resistant Organisms on the Skin with Early Preop Prep, http://www.sageproducts.com/products/ssi-prevention.cfm, 1 page, Oct. 31, 2008.

Sage Products, Inc., Preoperative Skin Preparation and Perioperative Oral Care for the Short-Term Ventilated Patient, http://www.sageproducts.com/products/ssi-vap-prevention.cfm, 1 page, Oct. 31, 2008.

Enturia, ChloraPrep, http://www.enturia.com/products/chloraPrepichloraPrep-product.html, pp. 1-3, Oct. 31, 2008.

McDonnell, G., Russell, A.D. Antiseptics and Disinfectants: Activity, Action, and Resistance. Clinical Microbiology Reviews, (1999) 12(1), pp. 149-179.

* cited by examiner

BLOOD CONTROL CATHETER WITH ANTIMICROBIAL NEEDLE LUBE

BACKGROUND OF THE INVENTION

The current invention relates to a lubricant for dermally invasive devices. In particular, the present invention relates to methods and systems whereby an antimicrobial lubricant is applied to the outer surface of a catheter device to prevent infection.

Catheters are commonly used for a variety of infusion therapies. For example, catheters are used for infusing fluids, such as normal saline solution, various medicaments, and total parenteral nutrition into a patient, withdrawing blood from a patient, as well as monitoring various parameters of the patient's vascular system.

Catheters are commonly introduced into the vasculature of a patient as part of an intravenous catheter assembly. The catheter assembly generally includes a catheter adapter, which supports the catheter, the catheter adapter being coupled to a needle hub which supports an introducer needle. The introducer needle is extended and positioned within the catheter such that a beveled portion of the needle is exposed beyond a tip of the catheter. The beveled portion of the needle is used to pierce the skin of the patient to provide an opening whereby to insert the needle in the vasculature of the patient. Following insertion and placement of the catheter, the introducer needle is removed from the catheter thereby providing intravenous access to the patient.

Catheter-related bloodstream infections are caused by the colonization of microorganisms in patients with intravascular catheters and I.V. access devices. These infections are an important cause of illness and excess medical costs, as approximately 250.000 catheter-related bloodstream infections occur in United States intensive care units each year. In addition to the monetary costs, these infections are associated with anywhere from 20,000 to 100,000 deaths each year.

Despite guidelines to help reduce healthcare associated infections (HAIs), catheter-related bloodstream infections continue to plague our healthcare system. The 10 most common pathogens (accounting for 84% of any HAIs) were coagulase-negative staphylococci (15%), *Staphylococcus aureus* (15%), *Enterococcus* species 12%), *Candida* species (11%), *Escherichia coli* (10%), *Pseudomonas aeruginosa* (8%), *Klebsiella pneumoniae* (6%), *Enterobacter* species (5%), *Acinetobacter baumannii* (3%), and *Klebsiella oxytoca* (2%). The pooled mean proportion of pathogenic isolates resistant to antimicrobial agents varied significantly across types of HAI for some pathogen-antimicrobial combinations. As many as 16% of all HAIs were associated with the following multidrug-resistant pathogens: methicillin-resistant *S. aureus* (8% of HAIs), vancomycin-resistant *Enterococcus faecium* (4%), carbapenem-resistant *P. aeruginosa* (2%), extended-spectrum cephalosporin-resistant *K. pneumoniae* (1%), extended-spectrumcephalosporin-resistant *E. coli* (0.5%), and carbanpenem-resistant *A. baumannii, K. pneumoniae, K. oxytoca*, and *E. coli* (0.5%) antimicrobial-resistant pathogens.

Impregnating catheters with various antimicrobial agents is one approach that has been implemented to prevent these infections. These catheters, however, have given less than satisfactory results. For example, these catheters are largely ineffective at preventing growth and colonization of pathogens on interior surfaces and components of a catheter assembly. In addition, some microbes have developed resistance to the various antimicrobial agents in the system.

Accordingly, there is a need in the art for dermally invasive devices having improved antimicrobial capabilities. Such methods and systems are disclosed herein.

BRIEF SUMMARY OF THE INVENTION

In order to overcome the limitations discussed above, the present invention relates to an antimicrobial lubricant matrix applied to a catheter device such that upon fully inserting the catheter device into a patient, the antimicrobial lubricant is interposed between the catheter and the dermal layers of the patient.

In some implementations, an antimicrobial formulation is provided as an insoluble lubricant material that is applied to an outer surface of an introducer needle as part of an intravenous catheter assembly. The lubricant material is applied so that as the needle is withdrawn through a blood control septum of the catheter assembly, a slit of the septum "squeegees" or otherwise removes a portion of the lubricant material from the outer surface of the needle. The removed lubricant material collects on the membrane and slit of the septum to provide a physical barrier between the slit and the vasculature of the patient. In some instances, a portion of the removed lubricant material is deposited within the slit, thereby further closing or sealing the slit.

In some instances, the lubricant material further comprises a lubricious agent. The lubricious agent reduces friction between the slit and the outer surface of the needle. As such, the needle may be removed through the septum in smooth and continuous manner without catching or otherwise damaging the septum's slit. The lubricious agent of the lubricant material may further reduce friction between the septum and an external Luer device that is inserted through the slit. The antimicrobial lubricant may be transferred to the Luer device as it is inserted through the slit, thereby killing any pathogens present thereon. In some implementations, the antimicrobial lubricant further includes an anti-thrombogenic agent to decrease the likelihood of blood clots within the catheter assembly.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
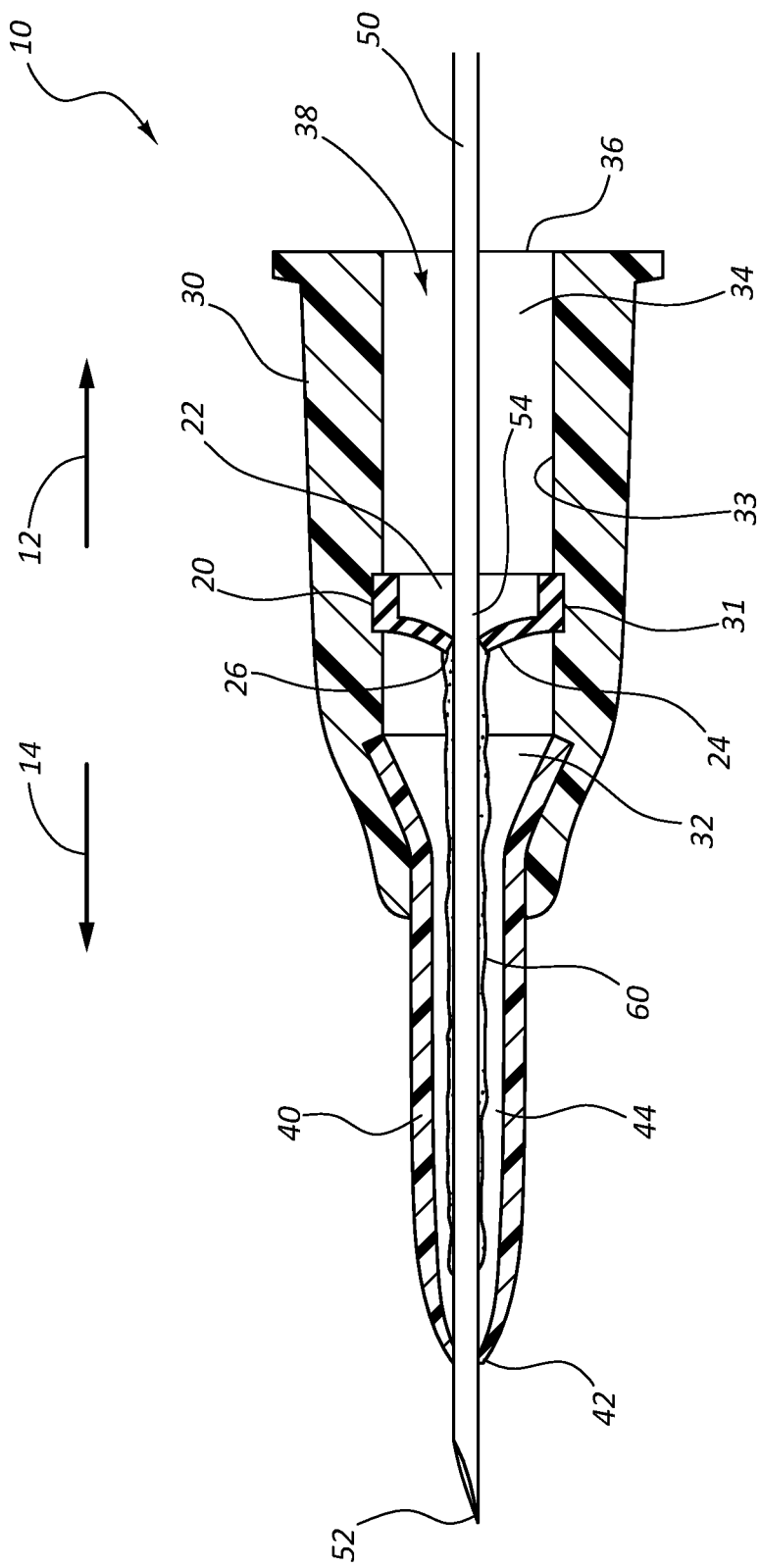
FIG. 1 is a cross-section view of a catheter assembly having a coated introducer needle positioned prior to being withdrawn from the catheter adapter in accordance with a representative embodiment of the present invention.

Referring now to FIG. 1, a catheter device assembly 10 is shown. In general, a catheter device assembly 10 in accordance with the present invention provides access to the vasculature of a patient, such as for infusion therapy procedures or blood collection. In some embodiments, catheter device system 10 comprises a catheter adapter 30 which supports a catheter tube 40. Catheter tube 40 extends outwardly from catheter adapter 30 and is in fluid communication therewith.

In some embodiments, catheter device system 10 further comprises a needle hub (not shown) which supports an introducer needle 50. Introducer needle 50 is threadedly positioned through catheter adapter 30 and catheter tube 40 such that a beveled tip 52 of needle 50 extends beyond catheter tip 42. Beveled tip 52 provides a cutting surface whereby to penetrate the patient's skin and provide access to the patient's vasculature. Once catheter 40 is fully inserted into the patient, introducer needle 50 is removed thereby providing intravenous access to the patient 20 via catheter 40 and catheter adapter 30.

In some embodiments, catheter adapter 30 further comprises a blood control septum 20. Blood control septum 20 is provided as a physical barrier to control the flow of blood and other fluids between the forward chamber 32 and the rearward chamber 34 of catheter adapter 30. For example, upon insertion of beveled tip 52 and catheter tip 42 into the patient's vein and the removal of the needle 50, blood from the patient flows through lumen 44 of catheter tube 40 and into forward chamber 32. The patient's blood is prevented from bypassing septum 20, thereby retaining the blood in forward chamber 32. Without blood control septum 20 in place, blood would flow into rearward chamber 34 and out of opening 36 in an uncontrolled manner. This would result in undesirable exposure of the user to the patient's blood. Accordingly, blood control septum 20 is positioned in fluid pathway 38 of catheter adapter 30 to prevent the user from being exposed to the patient's blood.

In some instances, blood control septum 20 is seated into an annular groove 31 that is provided in the inner surface 33 of catheter adapter 30. In some embodiments, blood control septum 20 comprises an outer diameter that is greater than an inner diameter of fluid pathway 38, and is slightly larger than the diameter of annular groove 31. Thus, blood control septum 20 is seated into annular groove 31 and is prevented from moving within fluid pathway 38 in proximal 12 and distal 14 directions. In other instances, the outer peripheral edge of blood control septum 20 is secured to inner surface 33 via an adhesive, plastic weld, or other mechanical connection (such as a retainer clip).

Blood control septum 20 may comprise any structural configuration which is capable of dividing fluid pathway 38 into forward and rearward chambers 32 and 34. For example, in some embodiments blood control septum 20 comprises a disc. In other embodiments, blood control septum 20 comprises a cylinder having a proximal opening 22 and a distal cap forming a membrane 24. In some embodiments, membrane 24 comprises a slit 26 or a plurality of slits which form a pathway through membrane 24. Slit 26 may be configured to permit passage of introducer needle 50 through septum 20.

The resilient or stretchy nature of septum 20 permits slits 26 to stretch and thereby accommodate passage of needle 50. In some instances, a seal or interface between slit 26 and the outer surface of needle 50 is sufficiently tight so that slit 26 prevents passage of fluid from forward chamber 32 to rearward chamber 34 when needle 50 is moved in proximal direction 12. Further, blood that is present on outer surface 54 of the portion of needle 50 located in forward chamber 32 is removed or "squeegeed" from outer surface 54 as needle 50 moved through slit 26 in proximal direction 12. Upon complete removal of needle 50 from slit 26, slit 26 self-closes, thereby further preventing fluid within forward chamber 32 from passing into rearward chamber 34.

Typically, the introducer needle 50 is coated with an oily lubricant that helps to reduce the system drag during needle removal. In some embodiments, the lubricant further comprises an antimicrobial agent forming an antimicrobial lubricant 60. The antimicrobial lubricant 60 is provided as a means for preventing colonization and growth of microbes and pathogens within catheter assembly 10. In some embodiments the antimicrobial lubricant 60 is applied to entire outer surface 54 of needle 50. In some instances, the antimicrobial lubricant 60 is applied to the portion of outer surface 54 that is located in forward chamber 32. During clinical usage, as the introducer needle is removed from the catheter, part of the antimicrobial lubricant 60 is removed or "squeegeed" from outer surface 54 as needle 50 moved through slit 26 in proximal direction 12, forming an antimicrobial barrier on the septum surface and within the slit 26. In this way, antimicrobial lubricant 60 acts as a barrier to prevent bacterial contamination of fluids the catheter.

In some embodiments, an antimicrobial lubricant is insoluable in most infusates and blood thus stay on the septum surfaces during multiple procedures, such as blood drawings, drug infusion, TPN procedures, as well as saline and heparin flushes. Therefore the antimicrobial lubricant can provide long lasting antimicrobial protection.

The formulations of the lubricant in this invention are comprised of a mixture or combination of one or more lubricants, and antimicrobial agents. In the mixture, the antimicrobial agents are uniformly and permanently distributed throughout the lubricant matrix.

In some embodiments, antimicrobial lubricant 60 comprises at least one of a water soluble lubricant, an insoluble lubricant, a viscous gel lubricant, a solid lubricant and a shapeable lubricant.

In some embodiments, antimicrobial lubricant 60 comprises oil lubricant. The oil lubricant can be polydimethyl siloxane, polytrifluoropropylmethyl siloxane, or a copolymer of dimethylsiloxane and trifluoropropylmethylsiloxane. The viscosity of the oil lubricant can be from 20 cp to 1,000,000 cp. In some embodiments, a solvent is added to the oil lubricant with very high viscosity to facilitate application of the antimicrobial lubricant.

Antimicrobial lubricant 60 may be applied to outer surface 54 by dipping, brushing, spraying, or any other compatible techniques known in the art. In some embodiments, excess antimicrobial lubricant 60 is applied to outer surface 54 prior to assembling needle 50 into catheter assembly 10. Needle 50 is inserted through septum 20 and into catheter 40 by providing an enlarged pathway through septum 20. In this way, antimicrobial lubricant 60 is not displaced from outer surface 54 during assembly.

Figure 7:
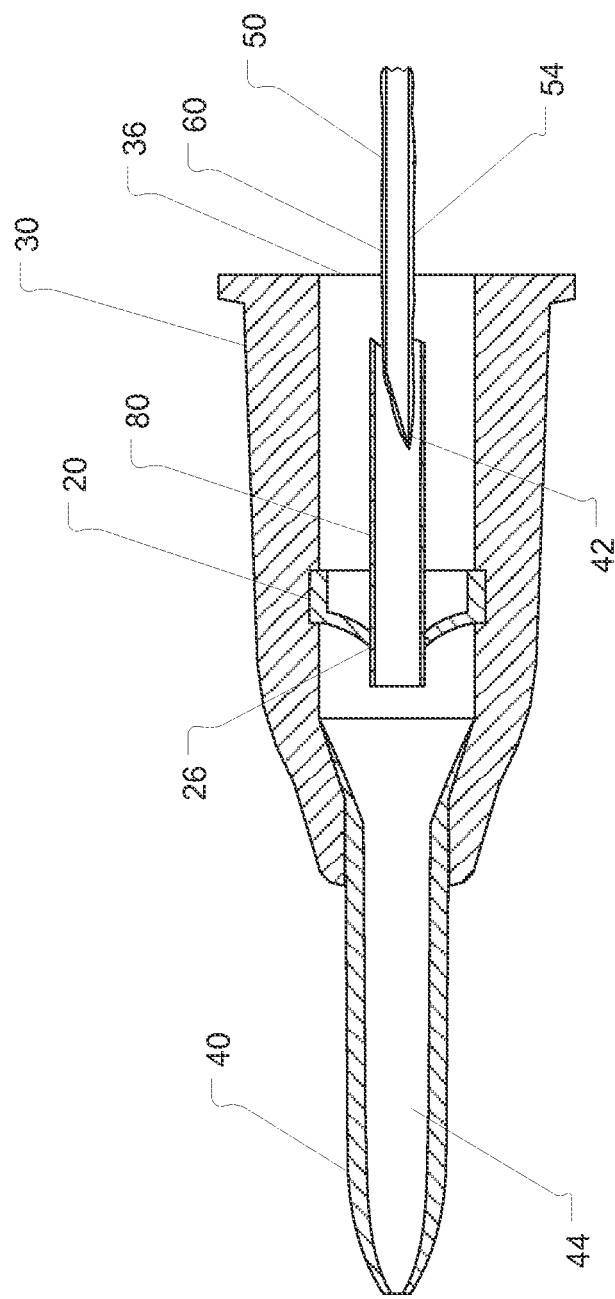
FIG. 7 is a cross-section view of a catheter assembly having a blood control septum with a threader to bias a slit in the septum into an enlarged, opened position in accordance with a representative embodiment of the present invention.

For example, in some embodiments as shown in FIG. 7, a threader 80 is inserted into opening 36 and through slit 26 of septum to bias slit 26 into an enlarged, opened position. The enlarged, opened position of slit 26 is generally greater than the diameter of the coated portion of introducer needle 50. The coated portion of introducer needle 50 is threaded through slit 26 via threader 80, and advanced through lumen 44 of catheter 40 until beveled tip 52 extends beyond catheter tip 42. Once in position, threader 80 is removed from slit 26 and catheter adapter 30. The resilient nature of septum 20 allows slit 26 to resume its closed position around outer surface 54.

Antimicrobial lubricant 60 generally comprises an antimicrobial or biocidal agent effective against various forms and strains of bacteria which may cause infection within a patient. The terms "biocidal agent" or "biocide," as used herein refer to an agent that destroys, inhibits and/or prevents the propagation, growth, colonization and multiplication of unwanted organisms. The term "organism" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms and mycobacteria. Specific examples of such organisms include the fungi *Aspergillus niger, Aspergillus flavus, Rhizopus nigricans, Cladosprorium herbarium, Epidermophyton floccosum, Trichophyton mentagrophytes, Histoplasma capsulatum*, and the like; bacteria such as *Pseudomanas aeruginosa, Escherichia coli, Proteus vulgaris, Staphylococcus aureus, Staphylococcus epidermis, Streptococcus faecalis, Klebsiella, Enterobacter aerogenes, Proteus mirabilis*, other gram-negative bacteria and other gram-positive bacteria, mycobactin and the like; and yeast such as *Saccharomcyces cerevisiae, Candida albicans*, and the like. Additionally, spores of microorganisms, viruses and the like are organisms within the scope of the present invention.

Antimicrobial or biocide agents suitable for use in the present invention include, but are not limited to phenol, quaternary ammonium, guanidine, taurolidine, parachloromethaxylenol, silver sulfadiazine, silver oxide, silver nitrate, pyridinium, benzalkonium chloride, cetrimide, benethonium chloride, cetylpyridinium chloride, dequalinium acetate, dequalinium chloride, and chloroxylenol. Further, in some embodiments lubricant 60 comprises a microbial agent selected from chlorhexidine base, chlorhexidine gluconate, chlorhexidine acetate, chlorhexidine hydrochloride, chlorhexidine dihydrochloride, dibromopropamidine, halogenated diphenylalkanes, carbanilide, salicylanilide, tetrachlorosalicylanilide, trichlorocarbanilide, and mixtures thereof. Still further, in some embodiments lubricant 60 comprises a microbial agent selected from chlorhexidine dihydrochloride, chlorhexidine gluconate, chlorhexidine acetate, chlorhexidine diacetate, triclosan, chloroxylenol, dequalinium chloride, benzethonium chloride, benzalkonium chloride, and combinations thereof. The antimicrobial agent can be solid particles that are insoluable in the lubricant or in liquid form. The antimicrobial agent is well mixed within the lubricant prior to application to introducer needles.

In some embodiments, lubricant 60 comprises one or more antimicrobial agents in an amount from approximately 0.01% (w/v) to approximately 10.0% (w/v) of lubricant 60. In other embodiments, lubricant 60 comprises one or more antimicrobial agents in an amount from approximately 0.001% (w/v) to approximately 5.0% (w/v) of lubricant 70. Further, in some embodiments lubricant 60 comprises one or more antimicrobial agents in an amount from approximately 0.01% to approximately 10.0% (w/v).

In some embodiments, lubricant 60 further comprises one or more fugitive solvents, such as tetrahydrofuran (THF), methylethylketone (MEK) and hexane solvents. In some embodiments, lubricant 60 comprises a fugitive solvent in an amount approximately equal to 70% (w/v) of lubricant 60. In other embodiments, lubricant 60 comprises two or more fugitive solvents.

In other embodiments, lubricant 60 comprises one or more alcohol components. Suitable alcohol components generally include a lower alcohol having between one and six carbons ($C_1$-$C_6$). In some embodiments, lubricant 60 comprises an alcohol component selected from the group consisting of ethyl alcohol, isopropanol, propanol, and butanol. In other embodiments, lubricant 60 comprises two or more lower alcohol components, for example a mixture of isopropyl alcohol and ethyl alcohol in a ratio of about 1:10 to about 1:1. Further, in some embodiments lubricant 70 comprises a mixture of more than two alcohol components.

In some embodiments, lubricant 60 comprises an alcohol component in an amount approximately equal to 40% (w/v) of lubricant 60. In other embodiments, lubricant 60 comprises an alcohol component in an amount from approximately 20% (w/v) to approximately 95% (w/v).

In some embodiments, antimicrobial lubricant 60 further comprises a lubricant, such as silicon oil. In some embodiments, introducer needle 50 is coated with a high viscosity antimicrobial lubricant 60 to reduce adhesion between the needle 50 and the catheter tip 42, as well as between the needle 50 and the septum 20. Upon withdrawing needle 50 from catheter 40 and septum 20, slit 26 of septum 20 rubs against the outer surface 54 of the needle 50, thereby removing excess lubricant 60, as shown in FIG. 2.

In some embodiments, antimicrobial lubricant 60 further comprises an anti-thrombogenic agent. An anti-thrombogenic agent is provided to decrease the likelihood of blood clotting within catheter assembly 10. In some instances, an anti-thrombogenic agent is provided to decrease the likelihood of blood clotting within forward chamber 32 or on any surface coated by antimicrobial lubricant 60.

Figure 2:
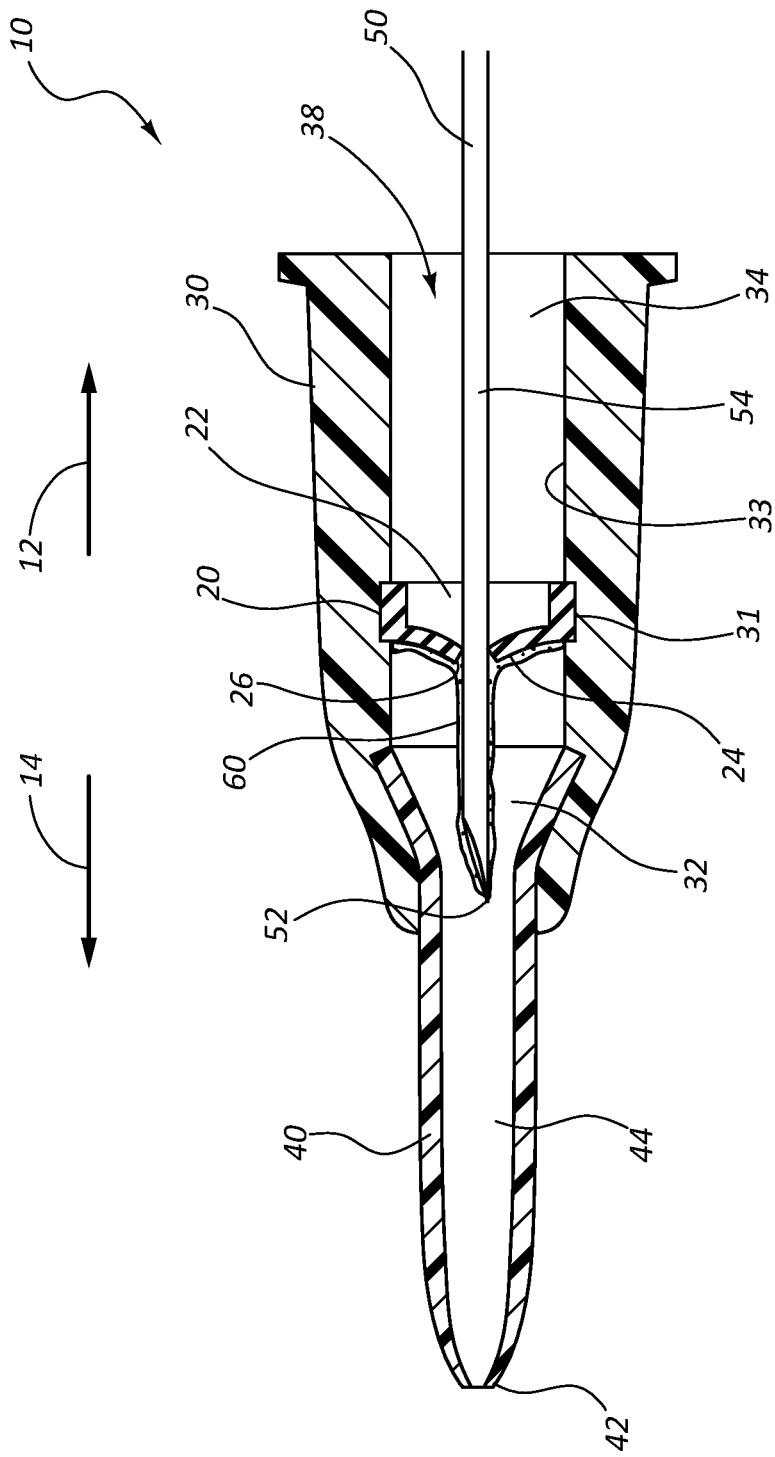
FIG. 2 is a cross-section view of a catheter assembly having a coated introducer needle partially withdrawn from the catheter, wherein an antimicrobial lubricant on the introducer needle has been partially removed from the introducer needle by the blood control septum in accordance with a representative embodiment of the present invention.

Referring now to FIG. 2, catheter assembly 10 is shown having introducer needle 50 partially withdrawn. In some embodiments, excess antimicrobial lubricant 60 is "squeegeed" or removed from outer surface 54 as needle 50 is withdrawn through slit 26 of septum 20 in proximal direction 12. Excess lubricant 60 collects within forward chamber 32 thereby providing a barrier between membrane 24 and forward chamber 32. This barrier will kill microorganisms that come in contact with and/or in close proximity of lubricant preventing microbial growth and colonization on membrane 24 and generally within forward chamber 32.

Figure 3:
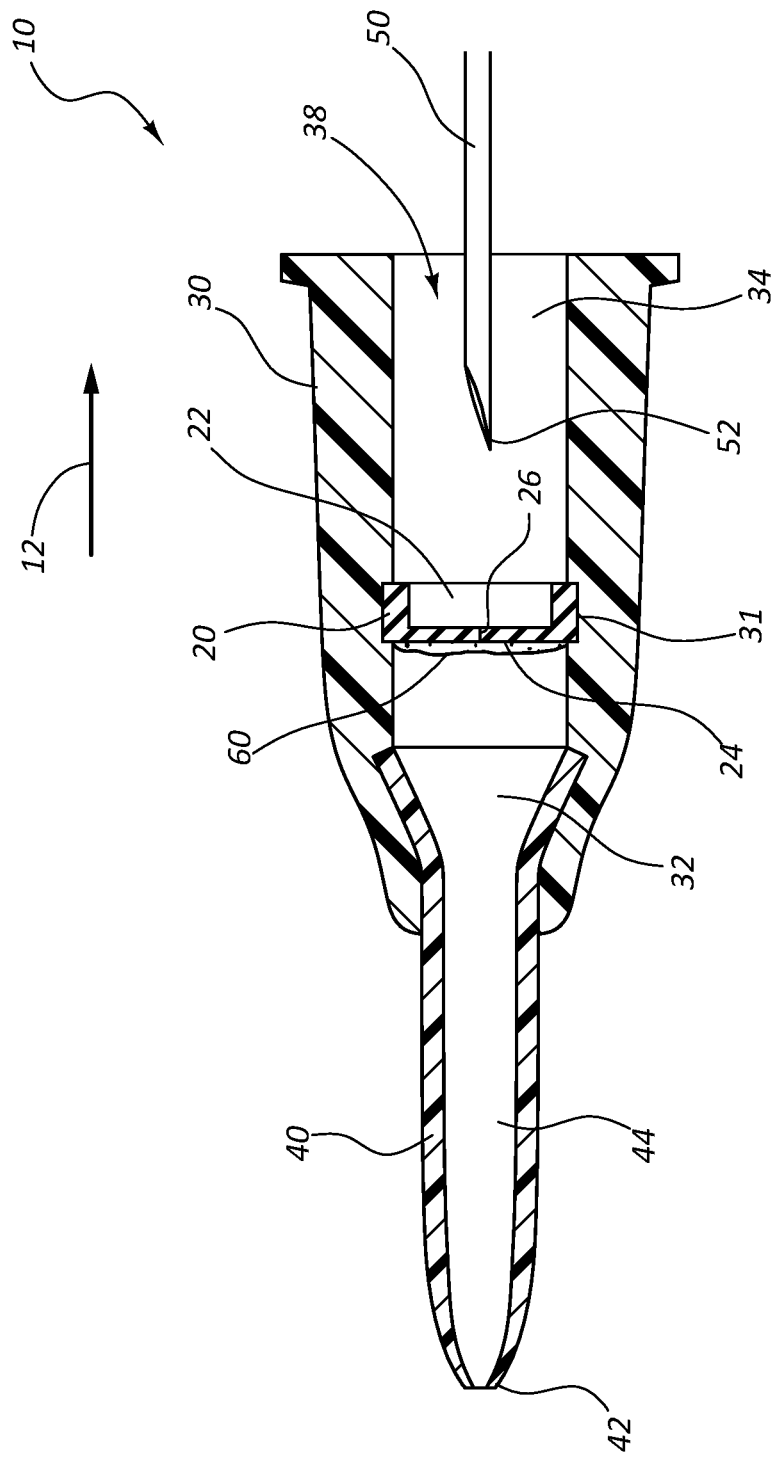
FIG. 3 is a cross-section view of a catheter assembly having a blood control septum that is coated with an antimicrobial material that was removed from the outer surface of an introducer needle by the blood control septum as the introducer needle was withdrawn from the catheter adapter in accordance with a representative embodiment of the present invention.

Upon complete withdrawal of introducer needle 50 from septum 20, slit 26 self-closes thereby providing a further physical barrier between forward and rearward chambers 32 and 34, as shown in FIG. 3. The barrier provided by excess antimicrobial lubricant 60 may further migrate to other surfaces in close proximity of the septum thus provide antimicrobial protection to the inside surfaces of the catheter beyond the septum.

Figure 4:
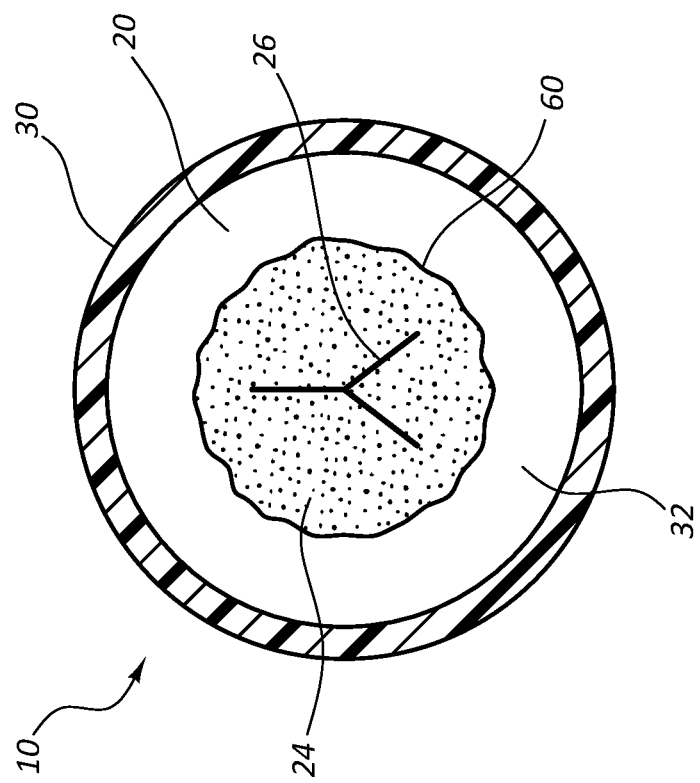
FIG. 4 is a cross-section end view of the blood control septum and deposited antimicrobial lubricant material following removal of the introducer needle in accordance with a representative embodiment of the present invention.

In some embodiments, slit 26 of blood control septum 20 comprises a tri-slit configuration, as shown in FIG. 4. Following removal of needle 50, excess antimicrobial lubricant 60 is deposited on membrane 24 thereby covering slit 26. Antimicrobial lubricant 60 prevents colonization and growth of pathogens on membrane 24.

Figure 5:
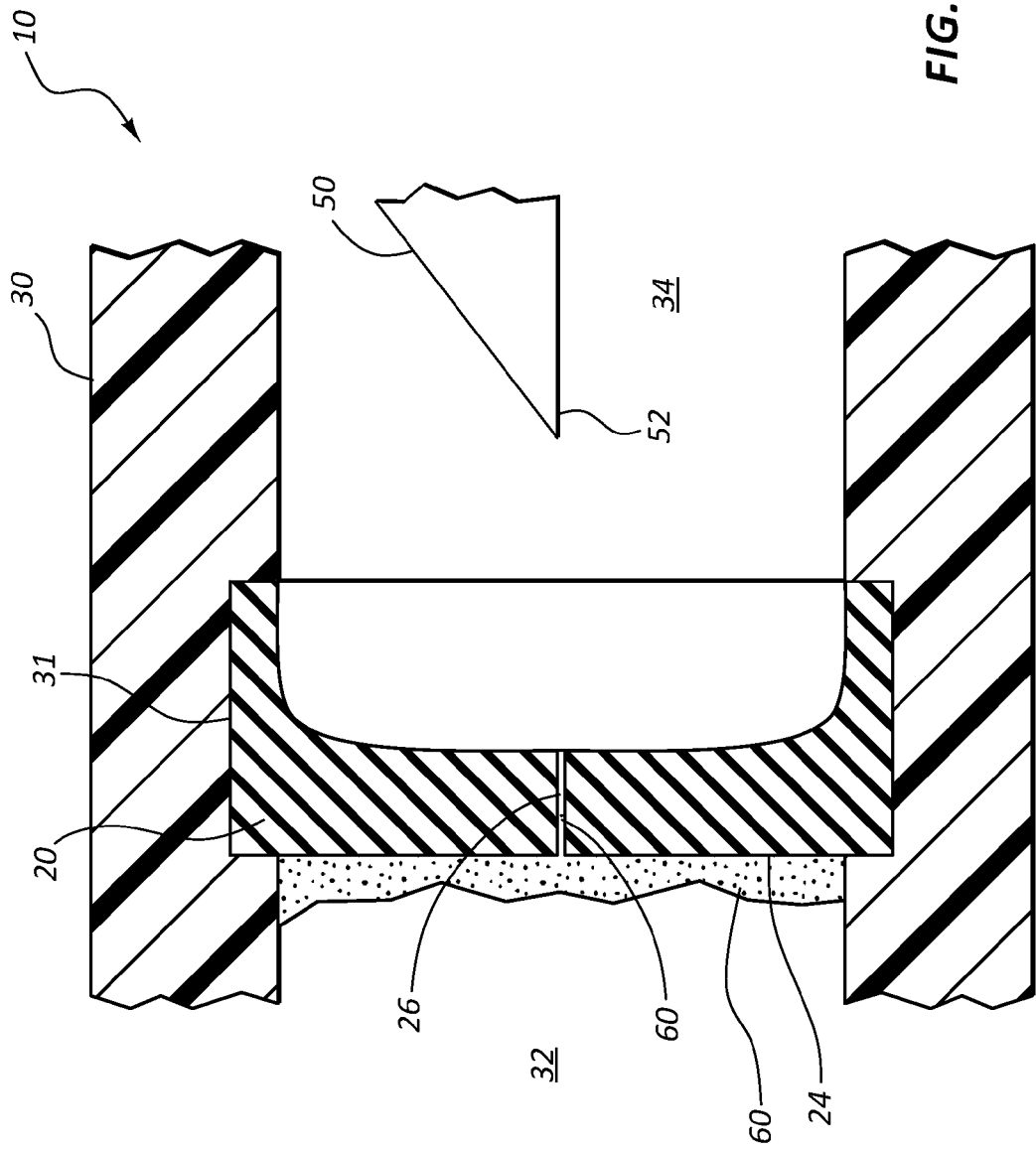
FIG. 5 is a detailed, cross-section view of the slit in the blood control septum following removal of the introducer needle, wherein residual antimicrobial lubricant material is deposited within the slit of the blood control septum in accordance with a representative embodiment of the present invention.

In some embodiments, excess antimicrobial lubricant 60 migrates into slit 26 thereby filling any gaps or openings in slit 26, as shown in FIG. 5. In this manner, excess antimicrobial lubricant 60 assists septum 20 in preventing flow of fluids between forward and rearward chambers 32 and 34.

Figure 6:
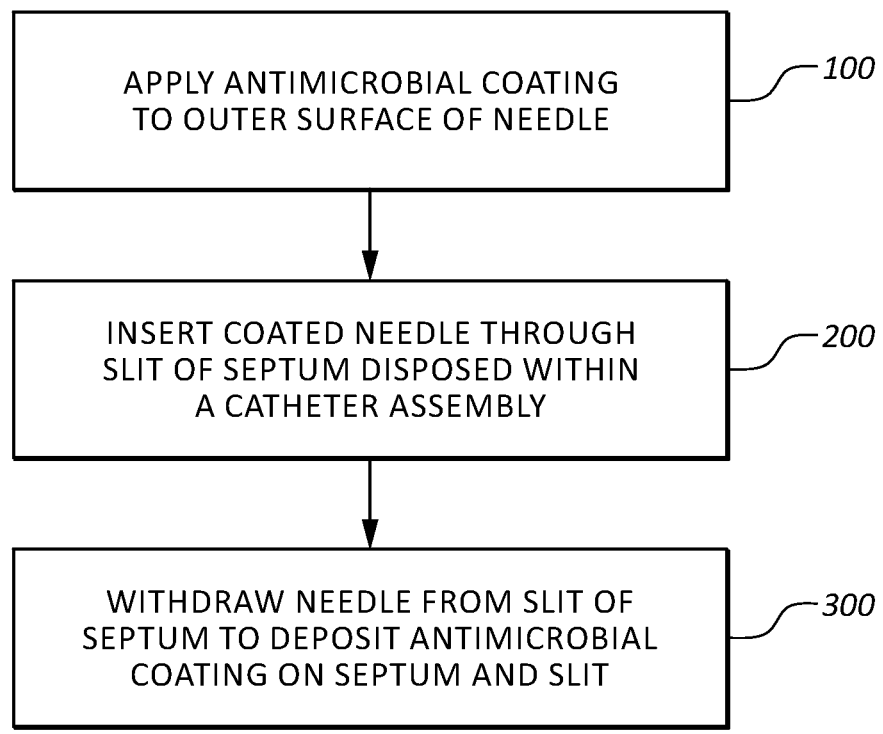
FIG. 6 is a flow chart demonstrating a method for lubricant a septum with an antimicrobial composition is accordance with a representative embodiment of the present invention.

Some implementations of the present invention further include a method for lubricant a septum of a blood control catheter with antimicrobial needle lube, as outline in FIG. 6. In some instances, a first step lubricant the septum comprises applying an antimicrobial lubricant to an outer surface of an introducer needle (at step 100). The coated needle is then inserted through the slit of a septum disposed within a catheter assembly (at step 200). In some instances, a threader is first inserted into the slit of the septum to provide an enlarged opening. In this manner, the antimicrobial lubricant is prevented from being displaced during the assembly of the device. Once positioned within the catheter assembly, the threader is removed from the slit and the device is ready for use.

The septum is coated as the needle is withdrawn from the septum and the catheter assembly device (at step 300). As the needle is withdrawn, the slit of the septum squeegees excess antimicrobial lubricant from the outer surface of the needle. This excess antimicrobial lubricant is deposited on membrane and slit portions of the septum. In some instances, excess antimicrobial lubricant is deposited within a forward chamber of the catheter assembly device to form an additional barrier between the septum and the vasculature of the patient.

The present invention may be embodied in other specific forms without departing from its structures, methods, or other essential characteristics as broadly described herein and claimed hereinafter. For example, the present invention may be applied to any dermally invasive device, such as needles, scalpels, trocars, endoscopes, stoma appliances, and the like. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly, comprising:
  a catheter adapter having a proximal end, a distal end, and a fluid pathway extending therebetween;
  a catheter having a distal end and a proximal end, the proximal end of the catheter being coupled to the distal end of the catheter adapter, the catheter having a lumen in fluid communication with the fluid pathway;
  a septum disposed within the fluid pathway thereby dividing the fluid pathway into a forward chamber and a rearward chamber, the septum having a slit;
  a needle having a base, a tip, and a body extending therebetween;
  an amount of an antimicrobial lubricant applied to an outer surface of the body of the needle; and
  a threader for forming a temporary pathway through the septum during assembly of the catheter assembly, the temporary pathway formed by the threader allowing the body of the needle to be inserted through the slit of the septum without substantially removing the amount of antimicrobial lubricant from the outer surface of the body of the needle, wherein after the needle is inserted through the slit of the septum and the threader is removed from the septum, the outer surface of the body of the needle is positioned distal to the septum such that, as the needle is withdrawn proximally through the septum, the septum removes the antimicrobial lubricant from the needle thereby depositing the antimicrobial lubricant on a distal side of the septum;
  wherein the threader is configured to be removed from the catheter assembly after the needle is inserted through the slit of the septum.

2. The catheter assembly of claim 1, wherein the slit comprises a tri-slit configuration.

3. The catheter assembly of claim 1, wherein the antimicrobial lubricant comprises at least one of a water soluble lubricant, an insoluble lubricant, a viscous gel lubricant, or a solid lubricant.

4. The catheter assembly of claim 1, wherein the antimicrobial lubricant comprises an oil lubricant such as polydimethyl siloxane, polytrifluoropropylmethyl siloxane, or a copolymer of dimethylsiloxane and trifluoropropylmethylsiloxane.

5. The catheter assembly of claim 1, wherein the antimicrobial lubricant comprises an antimicrobial agent.

6. The catheter assembly of claim 5, wherein the antimicrobial agent is at least one of chlorhexidine dihydrochloride, chlorhexidine gluconate, chlorhexidine acetate, chlorhexidine diacetate, triclosan, chloroxylenol, dequalinium chloride, benzethonium chloride, and benzalkonium chloride.

7. The catheter assembly of claim 4, wherein the antimicrobial lubricant further comprises at least one of a fugitive solvent component, an alcohol component, and an antimicrobial agent.

8. The catheter assembly of claim 4, wherein the antimicrobial agent is a non-alcohol based antimicrobial agent.

9. The catheter assembly of claim 7, wherein the polymer component is insoluble in water.

10. The catheter assembly of claim 7, wherein the polymer component is water soluble.

11. The catheter assembly of claim 7, wherein the antimicrobial agent is present in an amount from approximately 0.001% (w/v) to approximately 10.0% (w/v).

12. The catheter assembly of claim 7, wherein the antimicrobial agent is at least one of chlorhexidine dihydrochloride, chlorhexidine gluconate, chlorhexidine acetate, chlorhexidine diacetate, triclosan, chloroxylenol, dequalinium chloride, benzethonium chloride, and benzalkonium chloride.

13. The catheter assembly of claim 7, wherein the alcohol component comprises a lower alcohol having between one and six carbon atoms.

14. The catheter assembly of claim 7, wherein the alcohol component is present within the antimicrobial lubricant in an amount approximately equal to 20% (w/v).

15. The catheter assembly of claim 7, wherein the alcohol component comprises a mixture of isopropyl alcohol and ethanol, and is present within the antimicrobial lubricant in an amount from approximately 40% (w/v) to approximately 95% (w/v).

16. The catheter assembly of claim 7, wherein the fugitive solvent comprises an organic solvent that is present within the antimicrobial lubricant in an amount from approximately 20% (w/v) to approximately 95% (w/v).

17. A method for applying an antimicrobial lubricant to a septum of a catheter assembly, the method comprising:
    applying an antimicrobial lubricant to an outer surface of a needle;
    inserting a threader into a slit of the septum, the threader forming an enlarged opening through the septum;
    inserting the coated needle through the enlarged opening, the coated needle having a diameter less than the diameter of the enlarged opening such that the lubricant is not removed from the needle during insertion through the septum; and
    removing the threader from within the slit to allow the slit to seal around the needle such that, upon withdrawing the needle from the slit of the septum, the slit will remove a portion of the antimicrobial lubricant from the outer surface of the needle to form a deposit of the antimicrobial lubricant on the septum at a location proximate to the slit.

18. The method of claim 17, wherein the slit comprises a tri-slit configuration.

19. The method of claim 17, wherein the antimicrobial agent comprises at least one of a water soluble lubricant, an insoluble lubricant, a viscous gel lubricant, and a solid lubricant.

20. A method for depositing an antimicrobial agent on a septum of a catheter adapter after insertion of a catheter into a patient's vasculature, the method comprising:
    providing a catheter assembly comprising a catheter connected to a catheter adapter containing a septum positioned to divide the catheter adapter into a distal and proximal chamber;
    preparing the catheter assembly by inserting a threader into a slit of the septum to form an enlarged opening and inserting an antimicrobial lubricant coated needle through the enlarged opening, positioning the needle within the catheter, and removing the threader;
    inserting the needle and the catheter positioned around the needle into a patient's vasculature; and
    withdrawing the needle from the catheter such that, as the needle passes through the slit in the septum, the slit removes the antimicrobial lubricant from the needle thereby forming a deposit of the antimicrobial lubricant around the slit of the septum.

* * * * *